United States Patent
Park et al.

(10) Patent No.: US 12,257,460 B2
(45) Date of Patent: Mar. 25, 2025

(54) THERAPEUTIC ULTRASOUND GENERATION DEVICE, AND HANDPIECE FOR ULTRASOUND TREATMENT INCLUDING SAME

(71) Applicant: CLASSYS INC., Seoul (KR)

(72) Inventors: Si Hyung Park, Seoul (KR); Joon Hyun Choi, Seoul (KR)

(73) Assignee: CLASSYS INC., Seoul (KR)

( * ) Notice: Subject to any disclaimer, the term of this patent is extended or adjusted under 35 U.S.C. 154(b) by 213 days.

(21) Appl. No.: 17/783,545

(22) PCT Filed: Dec. 14, 2020

(86) PCT No.: PCT/KR2020/018229
§ 371 (c)(1),
(2) Date: Jun. 8, 2022

(87) PCT Pub. No.: WO2021/125718
PCT Pub. Date: Jun. 24, 2021

(65) Prior Publication Data
US 2023/0008673 A1    Jan. 12, 2023

(30) Foreign Application Priority Data
Dec. 16, 2019  (KR) .................. 10-2019-0167873

(51) Int. Cl.
*A61N 7/02* (2006.01)
*A61N 7/00* (2006.01)

(52) U.S. Cl.
CPC ........ *A61N 7/02* (2013.01); *A61N 2007/0034* (2013.01); *A61N 2007/0091* (2013.01)

(58) Field of Classification Search
CPC .............. A61N 7/02; A61N 2007/0034; A61N 2007/0091
See application file for complete search history.

(56) References Cited

U.S. PATENT DOCUMENTS 4,785,819 A    11/1988  Pearce
4,807,634 A     2/1989  Enjoji et al.
(Continued)

FOREIGN PATENT DOCUMENTS

CN    107440897 A    12/2017
CN    108465156 A     8/2018
(Continued)

OTHER PUBLICATIONS

International Search Report dated Apr. 1, 2021, issued in counterpart International Application No. PCT/KR2020/018229, w/English Translation. (7 pages).

*Primary Examiner* — Keith M Raymond
*Assistant Examiner* — Johnathan Maynard
(74) *Attorney, Agent, or Firm* — WHDA, LLP

(57) ABSTRACT

The present invention relates to a therapeutic ultrasound generation device, and a handpiece for ultrasound treatment including same. The therapeutic ultrasound generation device comprises: a cartridge housing unit; an ultrasonic transducer unit that is located in the cartridge housing unit, is disposed inclined with respect to a rotational central axis direction, and generates ultrasonic waves in the inclined direction; an inclined block unit that is located in the cartridge housing unit, has an inclined surface on the lower surface thereof, and supports the upper surface of the ultrasonic transducer unit such that the ultrasonic transducer unit is inclined with respect to the rotational central axis direction; and a rotating motor that rotates the inclined block unit. The therapeutic ultrasound generation device simplifies the structure of moving the focal point of the ultrasonic waves, generated by the ultrasonic transducer unit, in a circular shape on the same plane.

4 Claims, 9 Drawing Sheets

(56) References Cited

U.S. PATENT DOCUMENTS

| | | | |
|---|---|---|---|
| 5,687,729 A | 11/1997 | Schaetzle | |
| 2011/0009739 A1 | 1/2011 | Phillips et al. | |
| 2017/0079614 A1* | 3/2017 | Saeki | A61B 8/4461 |
| 2017/0303888 A1* | 10/2017 | Jung | A61B 8/42 |
| 2018/0353778 A1* | 12/2018 | Jeong | A61N 7/00 |
| 2019/0134430 A1 | 5/2019 | Jeong | |
| 2020/0015876 A1* | 1/2020 | Chou | A61B 34/30 |
| 2021/0275151 A1* | 9/2021 | Clark | A61B 8/4494 |

FOREIGN PATENT DOCUMENTS

| | | | | |
|---|---|---|---|---|
| EP | 3235543 A2 | 10/2017 | | |
| JP | 59-42971 U | 3/1984 | | |
| JP | 60-135034 A | 7/1985 | | |
| JP | 2004-49320 A | 2/2004 | | |
| KR | 10-1365946 B1 | 2/2014 | | |
| KR | 20160043471 A * | 4/2016 | | A45D 33/00 |
| KR | 10-1649899 B1 | 8/2016 | | |
| KR | 10-1677903 B1 | 11/2016 | | |
| KR | 10-2016-0139517 A | 12/2016 | | |
| KR | 10-2017-0062651 A | 6/2017 | | |
| KR | 10-2017-0064458 A | 6/2017 | | |
| KR | 10-2135733 B1 | 7/2020 | | |
| WO | 2017/095008 A1 | 6/2017 | | |

\* cited by examiner

FIG. 5
(a)
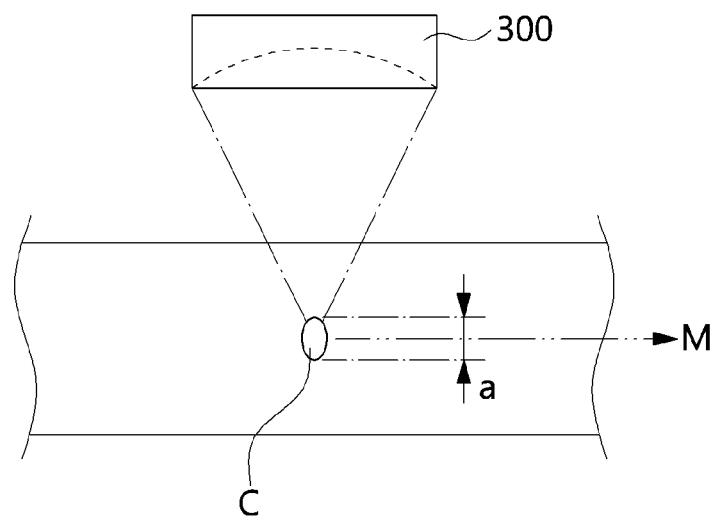
(a)
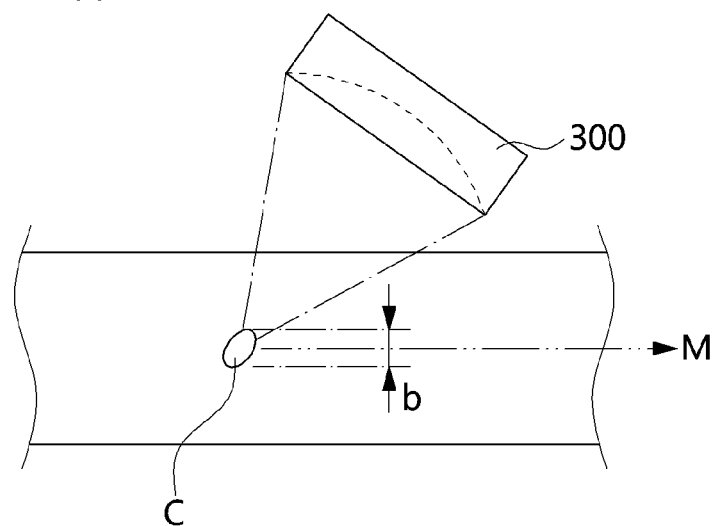

FIG. 6
(a)
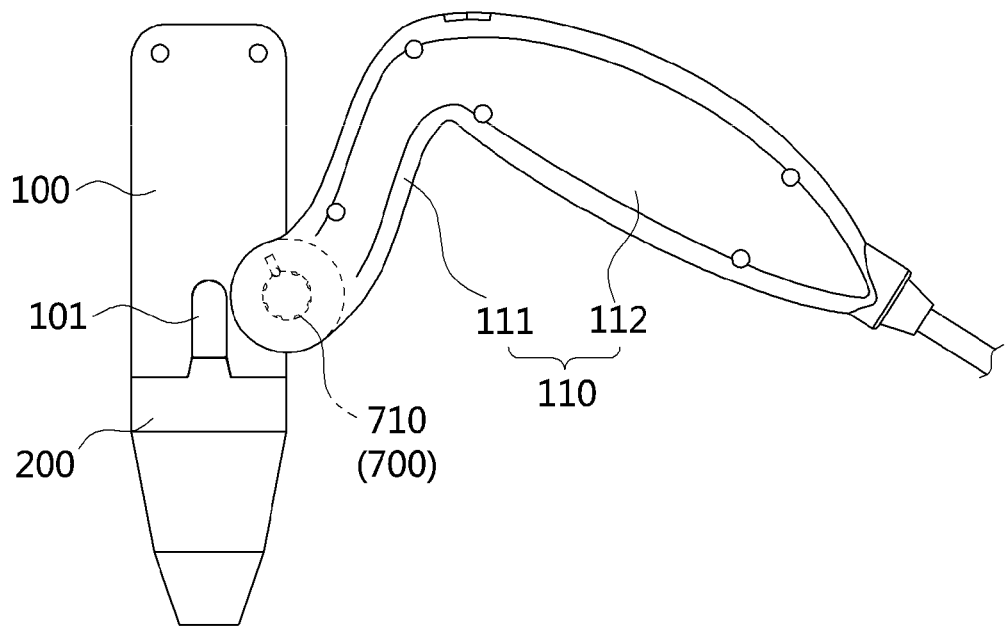
(b)
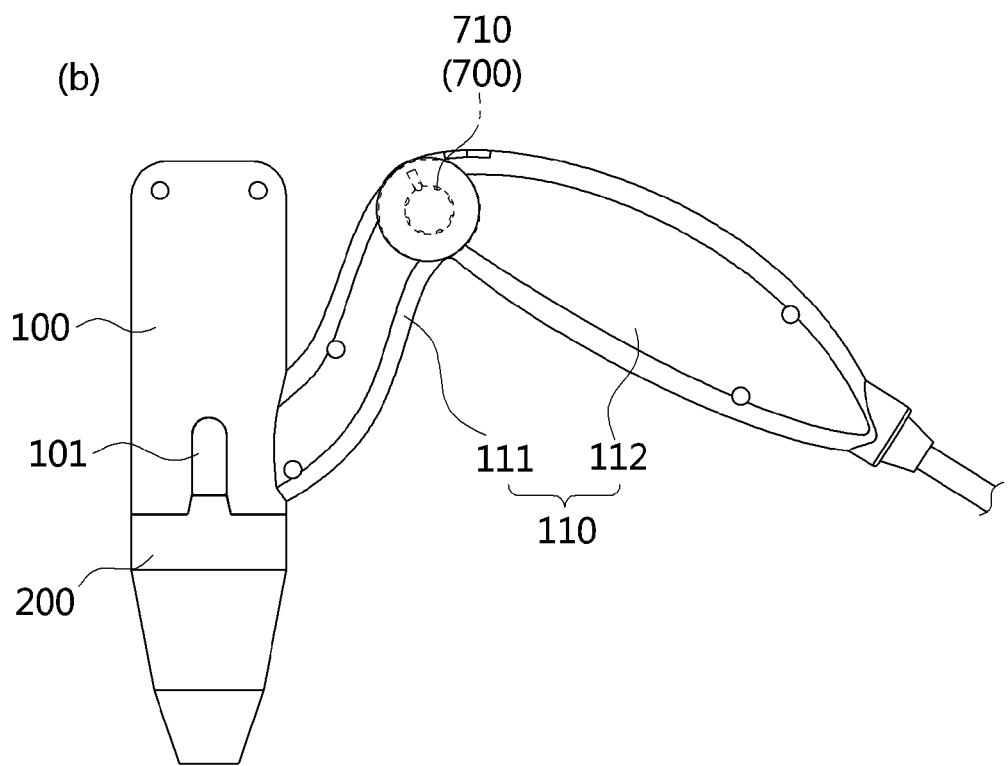

FIG. 8
(a)
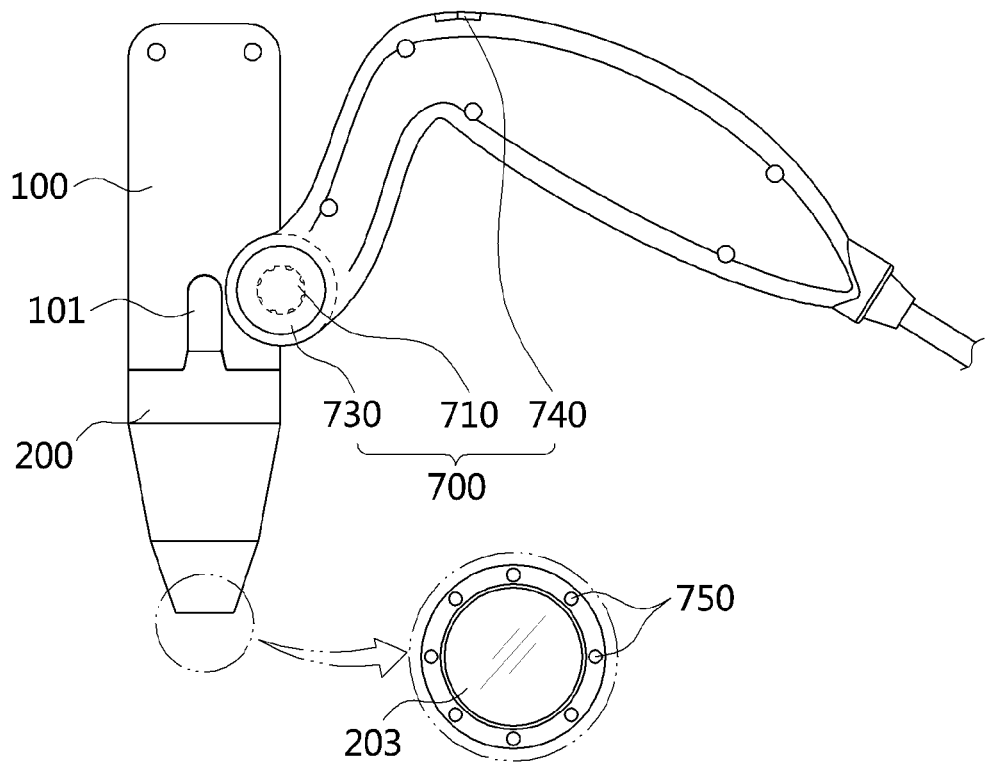
(b)
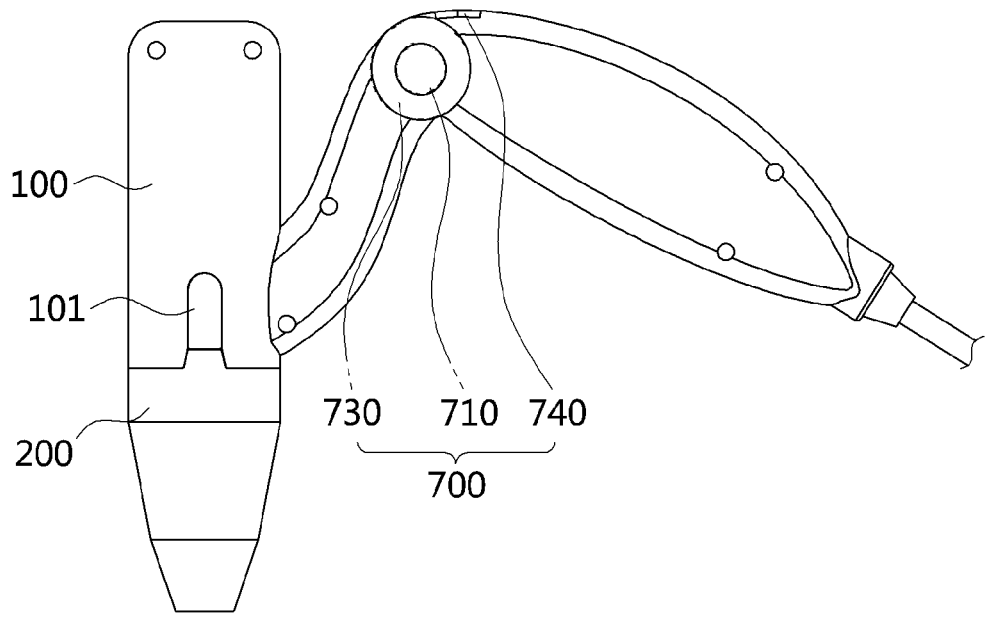

THERAPEUTIC ULTRASOUND GENERATION DEVICE, AND HANDPIECE FOR ULTRASOUND TREATMENT INCLUDING SAME

TECHNICAL FIELD

The present disclosure relates to a therapeutic ultrasound generation device, and to a handpiece for ultrasound treatment including the same. More particularly, the present disclosure relates to a therapeutic ultrasound generation device, and to a handpiece for ultrasound treatment including the same, the device being capable of miniaturizing a size of the handpiece for ultrasound treatment by simplifying a structure in which a focus of ultrasonic waves generated from an ultrasound generating unit is moved in a circular shape on the same plane.

BACKGROUND ART

Recently, as dietary life has become westernized, a rapid rise in obesity has become one of the major causes damaging health and beauty nationally. Accordingly, various diet programs and ultrasonic wave devices for treatment of obesity have been developed and are widely used.

An obesity treatment technique of a High Intensity Focused Ultrasound (HIFU) was originally used for the purpose of anticancer therapy by destroying cancer cells by selectively and noninvasively targeting tumors of internal organs, which were coagulated at high temperature. Later, Solta Medical of the USA developed a device called Liposonix in which a HIFU technique is applied and which was the first apparatus used for treatment of human abdominal obesity.

A process of fat-shattering by using the HIFU technique is to cause a tissue temperature to be raised to 65° C. to 100° C. at a moment when ultrasonic waves are focused on a designated point of a fat cell, thereby destroying the tissue.

An HIFU device induces coagulation necrosis of fat to occur noninvasively by focusing HIFU energy on a selected part without causing any harm on the skin surface, which is different from, for example, laser and high frequency RF equipment used in the dermatology field. The fat necrosed as such is naturally removed by a damaged portion restoration mechanism of our body.

As a known ultrasound obesity treatment device, Korean Patent No. 10-1365946 (Published on Feb. 24, 2014), having the title of 'HIGH INTENSITY FOCUSED ULTRASOUND GENERATING DEVICE FOR THE DEDUCTION OF FAT TISSUE' has been proposed.

In 'HIGH INTENSITY FOCUSED ULTRASOUND GENERATING DEVICE FOR THE DEDUCTION OF FAT TISSUE', a transducer is moved to a desired position in an X-axis direction and a Y-axis direction and then is driven by a pivot operation with respect to a shaft, and ultrasonic waves are permeated inside the skin.

However, in 'HIGH INTENSITY FOCUSED ULTRASOUND GENERATING DEVICE FOR THE DEDUCTION OF FAT TISSUE', ultrasonic waves are supplied to a curved surface (circular arc) due to the characteristics of the pivot operation when the ultrasonic waves are supplied by the pivot operation, and energy supplied to the skin is reduced and a focus depth is changed when the ultrasonic waves are moved to a periphery of the curved surface, so that there is a problem that treatment cannot be performed uniformly.

In order to solve this problem, the present applicant has been proposed Korean Patent No. 10-1649899 having the title of 'ULTRASONIC APPARATUS FOR TREATMENT'. In Korean Patent No. 10-1649899, there has been proposed a structure in which a focus rotational movement unit capable of moving a focus of ultrasonic waves generated from an ultrasound generation unit to be in a circular shape on the same plane is included, and the focus of the ultrasonic waves is formed in the circular shape having a constant radius at a uniform depth in skin and energy is uniformly and evenly applied within the radius, so that treatment performance is increased.

However, in Korean Patent No. 10-1649899 having the title of 'ULTRASONIC APPARATUS FOR TREATMENT', in a structure in which a plurality of protruding members that protrude at different heights is in contact with an upper surface of the ultrasound generation unit is provided, there is a problem that a limitation in reducing the size of the apparatus and in stably moving the focus of the ultrasonic waves generated from an ultrasonic transducer unit to be in a circular shape on the same plane.

DISCLOSURE

Technical Problem

Accordingly, the present disclosure has been made keeping in mind the above problems occurring in the related art, and an objective of the present disclosure is to provide a therapeutic ultrasound generation device, and to provide a handpiece for ultrasound treatment including the same, the device being capable of increasing an obesity treatment performance by moving a focus of ultrasonic waves in a circular shape at a uniform depth inside skin so that the ultrasonic waves evenly and uniformly penetrate the skin.

Another objective of the present disclosure is to provide a therapeutic ultrasound generation device, and to provide a handpiece for ultrasound treatment including the same, the hand piece being capable of being miniaturized in size by simplifying a structure in which a focus of ultrasonic waves generated from a ultrasonic transducer unit is moved in a circular shape on the same plane, the device being capable of performing ultrasound treatment on local areas of a patient's skin, such as a portion below the eyes.

Technical Solution

In order to achieve the above objective, according to an embodiment of the present disclosure, there is provided a therapeutic ultrasound generation device including: a cartridge housing unit; an ultrasonic transducer unit positioned in the cartridge housing unit and disposed inclined with respect to a direction of a rotational central axis direction, thereby being configured to generate ultrasonic waves in an inclined direction; an inclined block unit positioned in the cartridge housing unit, having an inclined surface on a lower surface thereof, and supporting an upper surface of the ultrasonic transducer unit, thereby positioning the ultrasonic transducer unit to be inclined with respect to the rotational central axis direction; and a rotating motor configured to rotate the inclined block unit.

In the present disclosure, a ball joint unit to which the ultrasonic transducer unit is rotatably coupled may be protrudingly positioned on a center of the inclined block unit, a plurality of support ball members configured to be rotated while supporting the upper surface of the ultrasonic transducer unit may be protrudingly positioned on the lower surface of the inclined block unit, and the ultrasonic transducer unit may be coupled to a ball body of the ball joint unit and the upper surface of the ultrasonic transducer unit may be supported while being in contact with the plurality of support ball members, so that the ultrasonic transducer unit may be positioned inclined.

According to an embodiment of the present disclosure, the therapeutic ultrasound generation device may further include a torsion bar member which has a first end portion connected to the ultrasonic transducer unit and which has a second end portion connected to the cartridge housing unit.

In the present disclosure, the torsion bar member may include: a first mounting unit mounted on the ultrasonic transducer unit; a second mounting unit mounted on an inner surface of the cartridge housing unit; and a torsion spring unit having opposite end portions thereof respectively connected to the first mounting unit and the second mounting unit, the torsion spring unit absorbing shock with torsional elasticity.

In the present disclosure, the torsion spring unit may be formed such that the torsion spring unit has at least one of a bent unit or a curved unit.

The ultrasonic transducer unit may be configured to be continuously inclined in all directions of 360 degrees with respect to the rotational central axis direction, so that a focus of ultrasonic waves generated from the ultrasonic transducer unit may be moved such that the focus is formed in a circular shape on the same plane.

In order to achieve the above objective, according to an embodiment of the present disclosure, there is provided a handpiece for ultrasound treatment, the handpiece including: an ultrasonic transducer unit; a cartridge housing unit in which the ultrasonic transducer unit is positioned therein; and a body housing unit to which the cartridge housing unit is detachably coupled.

According to an embodiment of the present disclosure, the handpiece may further include: an inclined block unit positioned in the cartridge housing unit, having an inclined surface on a lower surface thereof, and supporting an upper surface of the ultrasonic transducer unit, thereby positioning the ultrasonic transducer unit to be inclined with respect to a rotational central axis direction; and a rotating motor configured to rotate the inclined block unit, wherein the ultrasonic transducer unit may be disposed inclined with respect to the rotational central axis direction, thereby being configured to generate ultrasonic waves in an inclined direction.

In the present disclosure, a ball joint unit to which the ultrasonic transducer unit is rotatably coupled may be protrudingly positioned on a center of the inclined block unit, a plurality of support ball members configured to be rotated while supporting the upper surface of the ultrasonic transducer unit may be protrudingly positioned on the lower surface of the inclined block unit, and the ultrasonic transducer unit may be coupled to a ball body of the ball joint unit and the upper surface of the ultrasonic transducer unit may be supported while being in contact with the plurality of support ball members, so that the ultrasonic transducer unit may be positioned inclined.

According to an embodiment of the present disclosure, the handpiece may further include a torsion bar member which has a first end portion connected to the ultrasonic transducer unit and which has a second end portion connected to the cartridge housing unit.

In the present disclosure, the torsion bar member may include: a first mounting unit mounted on the ultrasonic transducer unit; a second mounting unit mounted on an inner surface of the cartridge housing unit; and a torsion spring unit having opposite end portions thereof respectively connected to the first mounting unit and the second mounting unit, the torsion spring unit absorbing shock with torsional elasticity.

In the present disclosure, the ultrasonic transducer unit may be configured to be continuously inclined in all directions of 360 degrees with respect to the rotational central axis direction, so that a focus of ultrasonic waves generated from the ultrasonic transducer unit may be moved such that the focus may be formed in a circular shape on the same plane.

In the present disclosure, a handle unit capable of being held by an operator's hand may be protrudingly positioned at a first side of the body housing unit, and the handle unit may include: a handle connection unit bent toward an upper portion of the body housing unit and positioned on the body housing unit; and a handle body curved from the handle connection unit and positioned downward.

In the present disclosure, a handle unit capable of being held by an operator's hand may be protrudingly positioned at a first side of the body housing unit, and the handpiece may further include a handle hinge unit positioned between the body housing unit and the handle unit or between divided portions when the handle unit is divided into two portions, the handle hinge unit being configured to rotate the body housing unit around a hinge shaft unit.

In the present disclosure, the handle hinge unit may include a rotation stopper unit configured to restrain a rotation angle of the handle unit that is rotated around the hinge shaft unit.

In the present disclosure, the rotation stopper unit may include: a plurality of restraining groove units positioned to be spaced apart from each other on an outer circumferential surface of the hinge shaft unit; and a stopper protrusion unit which protrudes to an inner circumferential surface of a shaft hole where the hinge shaft unit is positioned and which is inserted into one of the plurality of restraining groove units, the stopper protrusion unit being configured to be separated from the one of the plurality of restraining groove units and then to be moved to a next one of the plurality of restraining groove units in a rotational direction when a rotational force equal to or more than a preset rotational force is applied to the stopper protrusion unit.

In the present disclosure, the handle hinge unit may include: an angle adjustment motor configured to adjust an angle of the body housing unit by rotating the hinge shaft unit; and an angle adjustment switch unit positioned at the handle unit and configured to control an operation of the angle adjustment motor.

According to an embodiment of the present disclosure, the handpiece may further include a plurality of contact sensor units positioned at a lower surface of the cartridge housing unit and configured to sense whether a window unit of the cartridge housing unit is in contact with skin, wherein the angle adjustment motor may be connected to the plurality of contact sensor units, and may receive a contact signal sensed at the plurality of contact sensor units and may adjust the angle of the body housing unit, thereby allowing an entire surface of the window unit to be in close contact with the skin.

In the present disclosure, the handle hinge unit may further include a clearance bushing unit into which the hinge shaft unit is inserted therein and configured to allow the hinge shaft unit to be rotated when a rotational force equal to or more than a preset rotational force is applied to the clearance bushing unit.

In the present disclosure, the handle hinge unit may further include: a brake pad configured to brake a rotation of the hinge shaft unit; and a brake actuation knob unit configured to press the hinge shaft unit with the brake pad.

Advantageous Effects

In the present disclosure, energy is uniformly and evenly applied to a treatment area by moving a focus of ultrasonic waves in a plane at a uniform depth in the skin, and the focus of the ultrasonic waves is formed in a circular shape having a constant radius at the uniform depth in the skin, so that there is an effect that treatment performance is increased by uniformly and evenly applying the energy within the radius.

In addition, in the present disclosure, a structure in which a focus of ultrasonic waves generated from the ultrasonic transducer unit is moved in a circular shape on the same plane is simplified, and a size of the handpiece for ultrasound treatment is miniaturized, so that there is an effect that ultrasound treatment of local areas of a patient's skin, such as a portion below the eyes, is capable of being performed.

DESCRIPTION OF DRAWINGS

FIG. 5 shows schematic views comparing a comparative example and an embodiment of the therapeutic ultrasound generation device according to the present disclosure.

FIGS. 6 to 8 show views illustrating another embodiment of the handpiece for ultrasound treatment according to the present disclosure.

DESCRIPTION OF REFERENCE NUMERALS OF IMPORTANT PARTS

Figure 1:
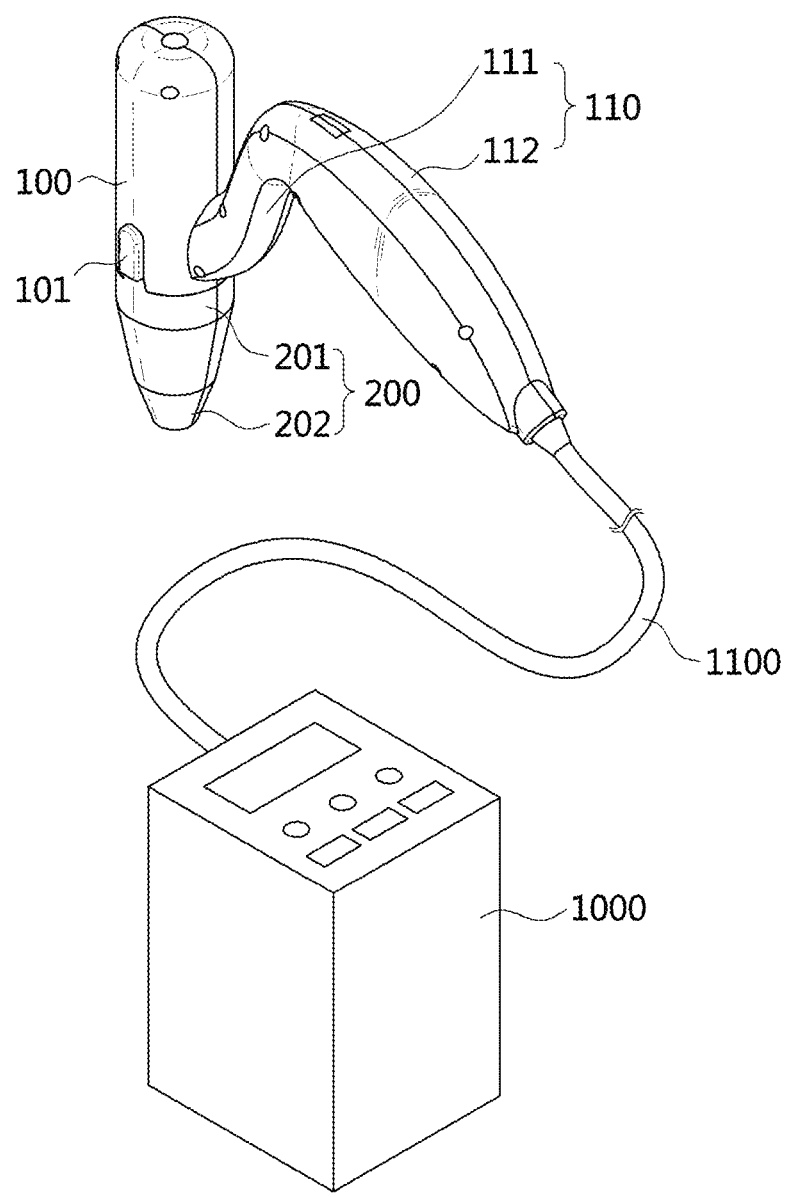
FIG. 1 is a perspective view illustrating an embodiment of a handpiece for ultrasound treatment according to the present disclosure.

100: body housing unit 101: cartridge locking unit
110: handle unit 111: handle connection unit
112: handle body 120: supply tube connection unit
130: discharge tube connection unit 140: second sensor connection terminal unit
200: cartridge housing unit 201: upper housing unit
202: cone housing unit 203: window unit
210: protruding tubular unit for supplying a medium 220: protruding tubular unit for discharging a medium
230: temperature detecting sensor unit 231: first sensor connection terminal unit
300: ultrasonic transducer unit 400: inclined block unit
410: block rotary shaft unit 411: connection shaft unit
420: ball joint unit 421: ball body
422: ball support shaft 430: support ball member
500: rotating motor 510: shaft adapter unit
600: torsion bar member 610: first mounting unit
620: second mounting unit 630: torsion spring unit
700: handle hinge unit 710: hinge shaft unit
720: rotation stopper unit 721: restraining groove unit
722: stopper protrusion unit 722a: stopper ball member
722b: stopper spring member 730: angle adjustment motor
740: angle adjustment switch unit 750: contact sensor unit
1000: control body

BEST MODE

Hereinbelow, the present disclosure will be described in more detail.

An exemplary embodiment of the present disclosure will be described in detail with reference to the accompanying drawings. Prior to the detailed description of the present disclosure, it should be noted that the terms and words used in the specification and the claims should not be construed as being limited to ordinary meanings or dictionary definitions. Therefore, the description proposed herein is just an exemplary embodiment for the purpose of illustrations only, not intended to limit the scope of the present disclosure, so it should be understood that other equivalents and modifications could be made thereto without departing from the scope of the present disclosure at the time at which the present application is filed.

Figure 2:
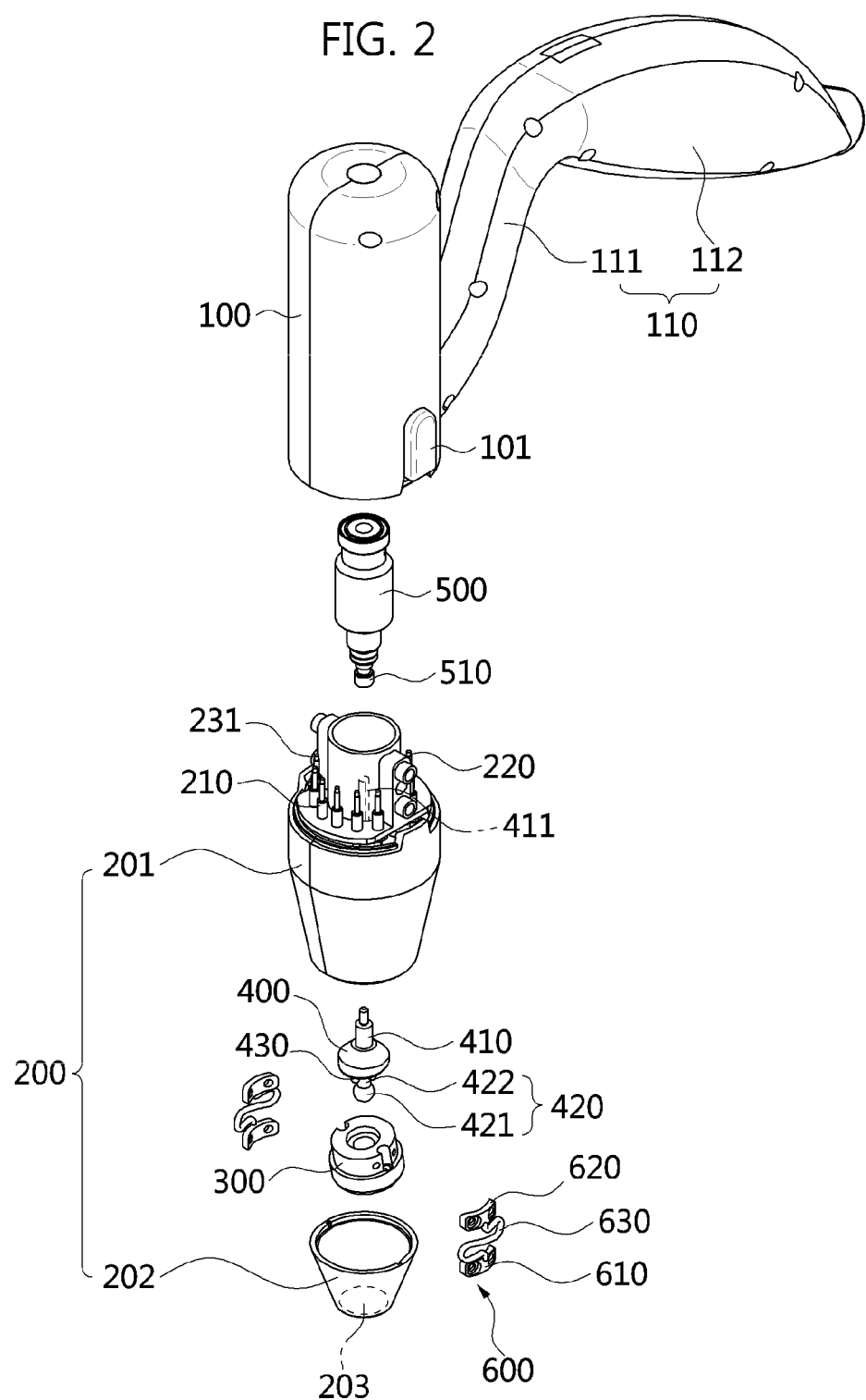
FIG. 2 is an exploded perspective view illustrating an embodiment of the handpiece for ultrasound treatment according to the present disclosure.
Figure 3:
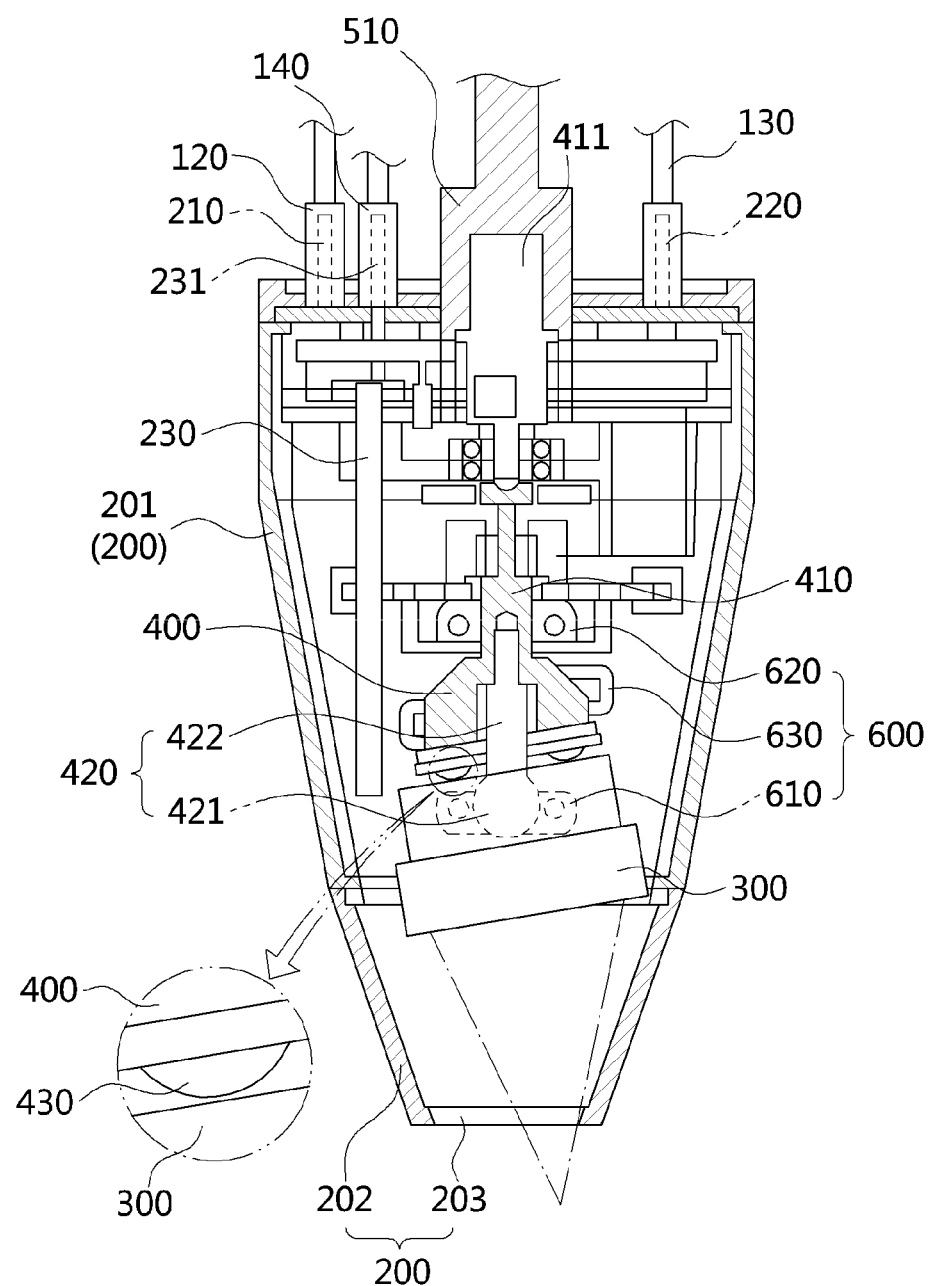
FIG. 3 is a cross-sectional view illustrating an embodiment of a therapeutic ultrasound generation device according to the present disclosure.

FIG. 1 is a perspective view illustrating a handpiece for ultrasound treatment according to an embodiment of the present disclosure, FIG. 2 is an exploded perspective view illustrating the handpiece for ultrasound treatment according to an embodiment of the present disclosure, and FIG. 3 is a cross-sectional view illustrating a therapeutic ultrasound generation device according to an embodiment of the present disclosure.

Referring to FIGS. 1 and 2, the handpiece for ultrasound treatment includes: a cartridge housing unit 200 in which an ultrasonic transducer unit 300 is positioned at an inner portion of the cartridge housing unit 200; and a body housing unit 100 to which the cartridge housing unit 200 is detachably coupled.

The handpiece for ultrasound treatment according to the present disclosure is connected to a control body 1000 via a cable body 1100 for a handpiece, the cable body 1100 including a power cable and both a medium supply line and a medium discharge line that are for circulating a medium in the cartridge housing unit 200. Further, the cable body 1100 for the handpiece and the control body 1000 may be realized in various forms of known examples of known ultrasonic treatment devices, so that a more detailed description thereof will be omitted.

A cartridge locking unit 101 on which the cartridge housing unit 200 is capable of being hung and fixed is positioned at the body housing unit 100. Further, the cartridge locking unit 101 is elastically supported by a spring, and thus a wedge-shaped catching unit is caught in a catching groove that is positioned inside the cartridge housing unit 200, so that a coupled state of the cartridge housing unit 200 is fixed. Furthermore, when the cartridge locking unit 101 is pressed, the catching unit is separated from the catching groove, and the cartridge housing unit 200 can be detached.

In addition to the cartridge locking unit 101, known locking structures capable of separating the cartridge housing unit 200 can be applied to the cartridge housing unit 200, and the cartridge housing unit 200 may be maintained in a state of being coupled to the body housing unit 100 or may be detached from the body housing unit 100, so that a more detailed description thereof will be omitted.

A handle unit 110 that can be held by hand of an operator is positioned at a first side of the body housing unit 100.

The handle unit 110 includes: a handle connection unit 111 bent toward an upper side of the body housing unit 100; and a handle body 112 curved downward from the handle connection unit 111.

The operator can hold the handle body 112 which is curved from the handle connection unit 111 and which integrally extends downward, so that the operator can perform an operation by easily contacting a window unit 203 of the cartridge housing unit 200 to the skin closely.

The handle unit 110 is designed such that a portion of the handle unit 110 having a shape which is bent upward and then which extends and which is curved downward, i.e., the handle body 112, is held. Therefore, a load applied to the operator during the operation may be minimized, and the operation may be performed with the window unit 203 of the cartridge housing unit 200 being capable of being easily in close contact with the skin.

Meanwhile, the therapeutic ultrasound generation device according to the present disclosure includes: the cartridge housing unit 200 in which the window unit 203 where ultrasonic waves are transmitted therethrough is positioned at a lower portion of the cartridge housing unit 200; and the ultrasonic transducer unit 300 positioned inside the cartridge housing unit 200 and configured to generate ultrasonic waves toward downward.

The window unit 203 is manufactured of a transparent material or a translucent material through which ultrasonic waves are transmitted. Further, since the window unit 203 is manufactured of known materials through which ultrasonic waves are transmitted, a more detailed description thereof will be omitted.

The cartridge housing unit 200 includes: an upper housing unit 201 detachably coupled to the body housing unit 100; and a cone housing unit 202 positioned at a lower side of the upper housing unit 201 and formed in a cone shape in which a diameter thereof gradually decreases toward downward.

Since the cartridge housing unit 200 includes the upper housing unit 201 formed in a cylindrical shape and includes the cone housing unit 202 formed in the cone shape in which the diameter thereof gradually decreases toward downward, a space capable of sufficiently locating a driving unit that is for rotating the ultrasonic transducer unit 300 is secured. In addition, since an area in contact with the skin via a lower surface of the cone housing unit 202 is lowered, the cartridge housing unit 200 may be easily in contact with local areas.

The window unit 203 is positioned at a lower surface of the cone housing unit 202, and the window unit 203 is formed in a size capable of performing ultrasound treatment by being in contact with the local areas of a patient's skin, such as a portion below the eyes of the patient.

The cartridge housing unit 200 has a structure in which an inner portion of the cartridge housing unit 200 is sealed, and the inner portion of the cartridge housing unit 200 is filled with an ultrasound transmission medium.

It should be noted that the ultrasound transmission medium is water as an example, and the ultrasound transmission medium may be realized in various forms.

The ultrasound transmission medium may not only serve to transmit ultrasonic waves but may also serve to cool the patient's skin through the window unit 203 that is in contact with the skin.

A protruding tubular unit 210 for supplying a medium and a protruding tubular unit 220 for discharging a medium that are for circulating the ultrasound transmission medium are protrudingly positioned at an upper surface of the cartridge housing unit 200.

In addition, an inclined block unit 400 having an inclined surface on a lower surface thereof is positioned inside the cartridge housing unit 200, and the inclined block unit 400 is rotated by a rotating motor 500.

On the inclined block unit 400, a block rotary shaft unit 410 detachably connected to a shaft of the rotating motor 500 protrudes upward.

The rotating motor 500 is positioned inside the body housing unit 100, and the block rotary shaft unit 410 is positioned such that an upper surface of the block rotary shaft unit 410 is exposed to an upper portion of the cartridge housing unit 200 or the block rotary shaft unit 410 protrudes the upper portion of the cartridge housing unit 200, so that the block rotary shaft unit 410 may be connected to the rotating motor 500 that is positioned inside the body housing unit 100.

The block rotary shaft unit 410 is rotatably positioned at an upper surface portion of the cartridge housing unit 200, and may be realized by using known sealing structures sealing a rotary shaft, so that a more detailed description thereof will be omitted.

The block rotary shaft unit 410 is provided with a connection shaft unit 411 that protrudes toward the upper surface of the cartridge housing unit 200, and the shaft of the rotating motor 500 is provided with a shaft adapter unit 510 into which the connection shaft unit 411 is inserted, thereby being connected to the block rotary shaft unit 410.

A shaft insertion unit that is open downward is positioned inside the shaft adapter unit 510 such that the connection shaft unit 411 is inserted into an inner portion of the shaft insertion unit. As an example, the connection shaft unit 411 is a shaft having a polygonal cross-sectional area, and the shaft insertion unit is an insertion groove unit having a polygonal shape that corresponds to the connection shaft unit 411.

A supply tube connection unit 120 and a discharge tube connection unit 130 that connect the protruding tubular unit 210 for supplying the medium and the protruding tubular unit 220 for discharging the medium to a medium circulating unit (not illustrated) which is positioned in the control body 1000 when the body housing unit 100 and the cartridge housing unit 200 are coupled to each other are positioned inside the body housing unit 100, the control body 1000 being configured to control an operation of the handpiece for ultrasound treatment.

The control body 1000 may be realized in various forms in a known ultrasound treatment device including a control unit configured to control an operation of a handpiece for ultrasound treatment and a medium circulating unit configured to circulate an ultrasound transmission medium, so that a more detailed description thereof will be omitted.

Although the medium circulating unit is not illustrated, the medium circulating unit may be realized in various forms by using a known cooling water circulating structure including a medium storage tank, a medium supply line unit connecting the medium storage tank to the supply tube connection unit 120, a medium discharge line unit connecting the medium storage tank to the discharge tube connection unit 130, a valve positioned at the medium supply line unit, a medium cooling unit positioned at the medium storage tank, and so on, so that a more detailed description thereof will be omitted.

The supply tube connection unit 120 is provided with a first protruding tube insertion unit into which the protruding tubular unit 210 for supplying the medium is inserted, and the discharge tube connection unit 130 is provided with a second protruding tube insertion unit into which the protruding tubular unit 220 for discharging the medium is inserted.

As an example, the protruding tubular unit 210 for supplying the medium is inserted into the first protruding tube insertion unit, and a flow path thereof is open, so that the protruding tubular unit 210 for supplying the medium is connected to the medium supply line unit. Further, as an example, the protruding tubular unit 220 for discharging the medium is inserted into the second protruding tube insertion unit, and a flow path thereof is open, so that the protruding tubular unit 220 for discharging the medium is connected to the medium discharge line unit.

Both the protruding tubular unit 210 for supplying the medium and the supply tube connection unit 120 and both the protruding tubular unit 220 for discharging the medium and the discharge tube connection unit 130 may be realized in various forms by applying a known tube connection structure including the valve which connects two tubes to each other and which is open when the two tubes are connected to each other.

In addition, the therapeutic ultrasound generation device according to the present disclosure further includes a temperature detecting sensor unit 230 configured to detect a temperature of the ultrasound transmission medium, and the temperature detecting sensor unit 230 includes a first sensor connection terminal unit 231 that protrudes to the upper surface of the cartridge housing unit 200 so as to be connected to the control body 1000.

A second sensor connection terminal unit 140 that connect the temperature detecting sensor unit 230 to the control body 1000 by being connected to the first sensor connection terminal unit 231 is positioned in the body housing unit 100, and a terminal insertion unit into which the first sensor connection terminal unit 231 is positioned at the second sensor connection terminal unit 140.

As an example, the first sensor connection terminal unit 231 is connected to the control unit of the control body 1000 via the second sensor connection terminal unit 140 by being inserted into the terminal insertion unit.

When the cartridge housing unit 200 is coupled to the body housing unit 100, the connection shaft unit 411 of the block rotary shaft unit 410 is inserted into the shaft insertion unit of the shaft adapter unit 510, and the block rotary shaft unit 410 and the shaft of the rotating motor 500 are connected to each other. Further, the protruding tubular unit 210 for supplying the medium is connected to the medium circulating unit of the control body 1000 by being inserted into the first protruding tube insertion unit of the supply tube connection unit 120, and the protruding tubular unit 220 for discharging the medium is connected to the medium circulating unit of the control body 1000 by being inserted into the second protruding tube insertion unit of the discharge tube connection unit 130. In addition, the temperature detecting sensor unit 230 is connected to the control unit of the control body 1000 by inserting the first sensor connection terminal unit 231 into the second sensor connection terminal unit 140.

Meanwhile, the block rotary shaft unit 410 protrudes on a center of the inclined block unit 400, so that the inclined block unit 400 is rotatably positioned inside the cartridge housing unit 200. Further, the inclined surface is positioned on the lower surface of the inclined block unit 400.

The inclined block unit 400 supports an upper surface of the ultrasonic transducer unit 300 with the inclined surface that is positioned at the lower surface of the inclined block unit 400, thereby maintaining the ultrasonic transducer unit 300 to be in an inclined state.

A ball joint unit 420 to which the ultrasonic transducer unit 300 is rotatably coupled protrudes and is positioned on the center of the inclined block unit 400.

The ball joint unit 420 includes a ball body 421 rotatably inserted into the upper portion of the ultrasonic transducer unit 300 and a ball support shaft 422 which protrudes from an upper portion of the ball body 421 and which is connected to the inclined block unit 400.

An upper end portion of the ball support shaft 422 is fixed to the center of the inclined block unit 400, and allows the ultrasonic transducer unit 300 to be continuously inclined in all directions of 360 degrees by a rotation of the inclined block unit 400 around the ball body 421.

A plurality of support ball members 430 that is configured to be rotated while supporting the upper surface of the ultrasonic transducer unit 300 is protrudingly positioned on the lower surface of the inclined block unit 400. Further, a part of each of the plurality of support ball members 430 is rotatably inserted into the inclined block unit 400 and is positioned inside the inclined block unit 400, and a rest part of each of the plurality of support ball members 430 protrudes and supports the upper surface of the ultrasonic transducer unit 300.

The plurality of support ball members 430 protrudes to the same height toward the lower surface of the inclined block unit 400, so that the ultrasonic transducer unit 300 is inclined at the same angle as an angle of the inclined surface. Further, when the ultrasonic transducer unit 300 is in the inclined state, all of the support ball members 430 are stably in contact with and supporting the upper surface of the ultrasonic transducer unit 300.

The ultrasonic transducer unit 300 is coupled to the ball body 421, so that the ultrasonic transducer unit 300 is positioned to be inclined while the upper surface of the ultrasonic transducer unit 300 is in contact with and supported by the plurality of support ball members 430.

The plurality of support ball members 430 are spaced apart from the center of the inclined block unit 400 at a predetermined distance in a circumferential direction. That is, the plurality of support ball members 430 are disposed radially from the center of the inclined block unit 400, thereby stably supporting the upper surface of the ultrasonic transducer unit 300 that is continuously inclined in all directions of 360 degrees.

When the inclined block unit 400 is rotated by the rotating motor 500, the ultrasonic transducer unit 300 is continuously inclined in all directions of 360 degrees by the inclined block unit 400 that is rotated.

Meanwhile, in an embodiment of the therapeutic ultrasound generation device according to the present disclosure, a structure in which the ultrasonic transducer unit 300 is continuously inclined in all directions of 360 degrees by both the inclined block unit 400 and the support ball members 430 that are positioned at the lower surface of the inclined block unit 400 is miniaturized.

In an embodiment of the therapeutic ultrasound generation device according to the present disclosure, a torsion bar member 600 having a first end portion connected to the ultrasonic transducer unit 300 and having a second end portion connected to the cartridge housing unit 200 may be further included.

The torsion bar is configured to absorb vibration that is generated when the ultrasonic transducer unit 300 is continuously inclined in all directions of 360 degrees, thereby securing an operation stability of the ultrasonic transducer unit 300.

Since the torsion bar is configured to absorb vibration that is generated when the ultrasonic transducer unit 300 is continuously inclined in all directions of 360 degrees, the operation stability of the ultrasonic transducer unit 300 may be secured even if a structure in which the ultrasonic transducer unit 300 is continuously inclined in all directions of 360 degrees is miniaturized.

When the structure is miniaturized, a radius in which the ultrasonic transducer unit 300 is continuously inclined in all directions of 360 degrees is decreased, and shock to the ultrasonic transducer unit 300 is repeated in a short cycle, so that vibration may be generated. Accordingly, the torsion bar member 600 uses torsional elasticity and absorbs shock that is generated when the ultrasonic transducer unit 300 is continuously inclined in all directions of 360 degrees in a short radius, thereby stably moving a focus of ultrasonic waves to form a circular shape on the same plane when the ultrasonic transducer unit 300 is continuously inclined in all directions of 360 degrees.

The torsion bar member 600 includes a first mounting unit 610 mounted on the ultrasonic transducer unit 300, a second mounting unit 620 mounted on an inner surface of the cartridge housing unit 200, and a torsion spring unit 630 having opposite end portions thereof respectively connected to the first mounting unit 610 and the second mounting unit 620.

The torsion spring unit 630 is formed such that the torsion spring unit 630 has at least one of a bent unit or a curved unit, thereby being capable of absorbing shock through the torsional elasticity.

As an example, the torsion spring unit 630 may be formed in a shape such as an S shape, a C shape, and so on, and has a length capable of absorbing corresponding shock that is generated when the ultrasonic transducer unit 300 is continuously inclined in all directions of 360 degrees while the ultrasonic transducer unit 300 has the same angle on the basis of the rotational central axis direction.

The torsion bar member 600 may include a plurality of torsion bar members 600. As an example, a pair of the torsion bar members 600 is positioned to be facing each other on a side surface of the ultrasonic transducer unit 300.

By providing the pair of torsion bar members 600 that are positioned to be facing each other, the operation stability of the ultrasonic transducer unit 300 may be further secured.

Figure 4:
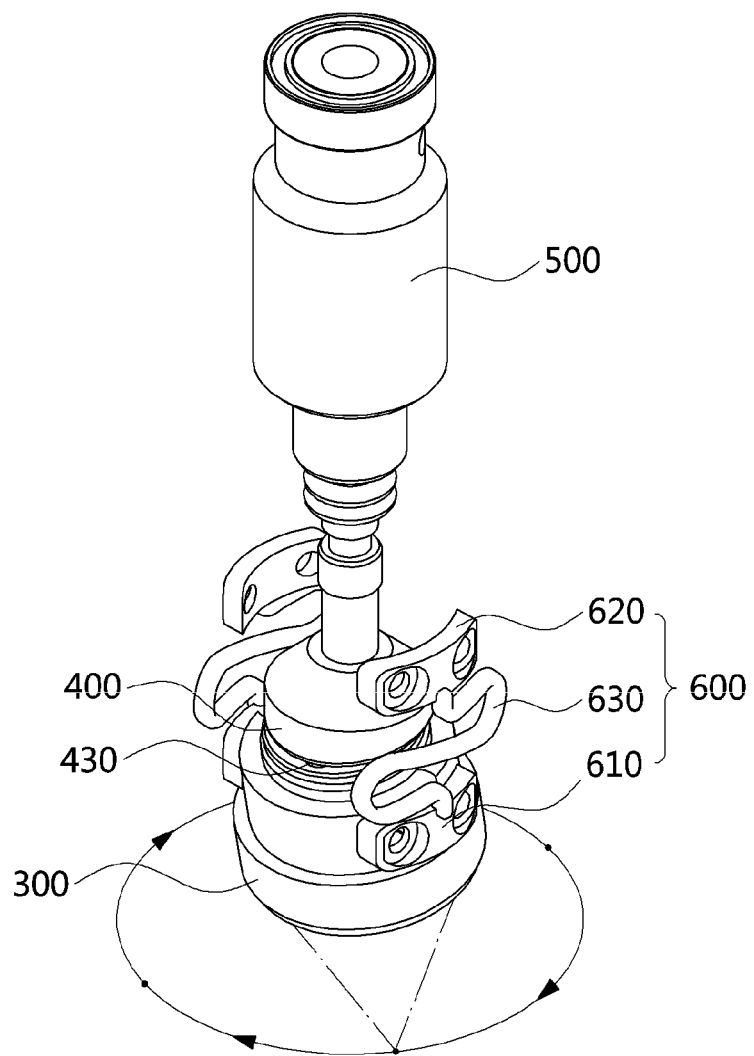
FIG. 4 is a view illustrating an operation example of the therapeutic ultrasound generation device according to the present disclosure.

FIG. 4 is a view illustrating an operation example of the therapeutic ultrasound generation device according to the present disclosure. Referring to FIGS. 3 and 4, in a state in which the ball body 421 of the ball joint is rotatably coupled to the ultrasonic transducer unit 300, the ultrasonic transducer unit 300 is in contact with and supported by the plurality of support ball members 430 that protrudes on the inclined surface of the inclined block unit 400, and is positioned to be inclined at an angle equal to an inclination of the inclined surface.

In this state, when the inclined block unit 400 is rotated by the rotating motor 500, the ultrasonic transducer unit 300 is continuously inclined in all directions of 360 degrees around the ball body 421. At this time, a focus of ultrasonic waves generated from the ultrasonic transducer unit 300 is moved to form a circular shape on the same plane.

In addition, since the torsion bar member 600 uses torsional elasticity so as to absorb vibration that is generated when the ultrasonic transducer unit 300 is continuously inclined in all directions of 360 degrees, a focus of ultrasonic waves may be stably moved while forming a circular shape on the same plane.

That is, the ultrasonic transducer unit 300 is continuously inclined in all directions of 360 degrees around the ball body 421, thereby stably moving the focus to form a circular shape on the same plane.

In the therapeutic ultrasound generation device according to the present disclosure, a focus of ultrasonic waves is formed in a circular shape having a constant radius at a uniform depth in the skin, so that energy is uniformly and evenly applied within the radius and a treatment performance may be further increased.

FIG. 5 shows schematic views comparing a comparative example and an embodiment of the therapeutic ultrasound generation device according to the present disclosure. FIG. 5A is a view illustrating the comparative example of the present disclosure in which the ultrasonic transducer unit emits ultrasonic waves in a direction perpendicular to the skin so that the ultrasonic waves are focused at a preset reference depth M in the skin. FIG. 5B is a view illustrating an embodiment of the present disclosure in which a focus C of ultrasonic waves at the reference depth M is formed since the ultrasonic transducer unit 300 is inclined with respect to a rotational central axis direction and the focus is formed at the preset reference depth M in the skin.

A focus of ultrasonic waves within the skin is formed in an oval shape. Therefore, it is preferable that a center of the focus is positioned at the preset reference depth M. Further, when the ultrasonic waves are focused as much as possible around the reference depth M, a therapeutic effect may be increased.

In FIG. 5A, in a situation in which the ultrasonic transducer unit 300 emits ultrasonic waves in a direction perpendicular to the skin such that the ultrasonic waves are focused at the preset reference depth M in the skin, a focus formed in an oval shape is positioned in a vertical direction, and a height of the focus is maximized.

However, as illustrated in FIG. 5B, in an embodiment of the present disclosure, ultrasonic waves are emitted to the skin while the ultrasonic transducer unit 300 is in the inclined state, and the focus C is positioned to be inclined at the reference depth M in the skin. Therefore, when an embodiment of the present disclosure is compared with the comparative example of the present disclosure illustrated in FIG. 5A, the height of the focus is reduced, and there is an effect that the focus is more concentrated and gathered on the reference depth M.

That is, in the therapeutic ultrasound generation device according to the present disclosure, by using a structure in which the ultrasonic transducer unit 300 is continuously inclined in all directions of 360 degrees, the focus C of ultrasonic waves forms a circular shape while being in the inclined state, and is moved on the same plane. Therefore, there is an effect that the focus is more concentrated and gathered on the reference depth M, and a skin treatment effect may be more increased.

Figure 7:
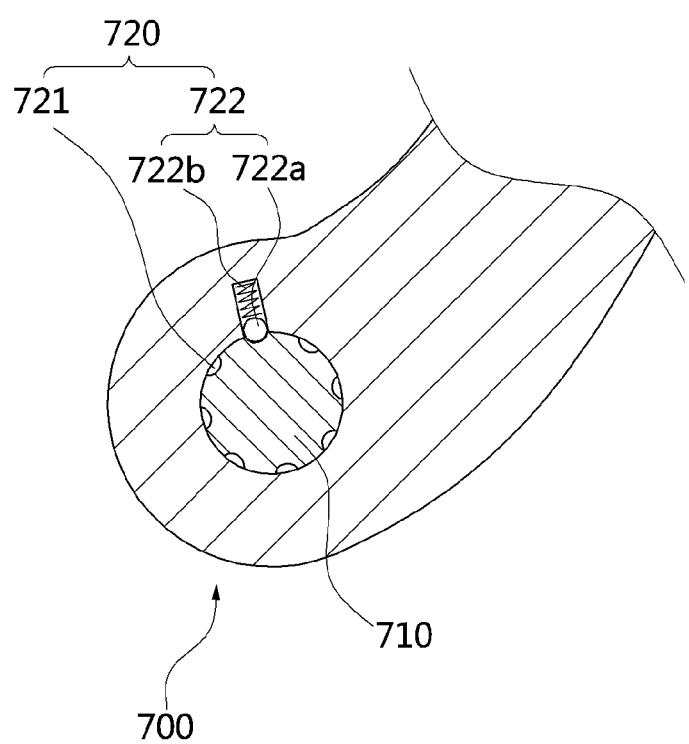

Meanwhile, FIGS. 6 to 8 are views illustrating another embodiment of the handpiece for ultrasound treatment according to the present disclosure. Referring to FIGS. 6 to 8, the handpiece for ultrasound treatment according to the present disclosure may further include a handle hinge unit 700 positioned between the body housing unit 100 and the handle connection unit 111 or between the handle connection unit 111 and the handle body 112, the handle hinge unit 700 being configured to rotate the body housing unit 100, thereby being capable of adjusting an angle of the body housing unit 100.

That is, the handle hinge unit 700 may be positioned between the body housing unit 100 and the handle unit 110, or may be positioned between divided portions when the handle unit 110 is divided into two portions.

FIG. 6A and FIG. 8A are views illustrating an example in which the handle hinge unit 700 is positioned between the body housing unit 100 and the handle connection unit 111, and FIG. 6B and FIG. 8B are views illustrating an example in which the handle hinge unit 700 is positioned between the handle connection unit 111 and the handle body 112.

By using the handle hinge unit 700, the operator can rotate the body housing unit 100 according to a treatment area so that the window unit 203 of the cartridge housing unit 200 can be completely in close contact with the treatment area, so that a treatment convenience is secured. In addition, an accident such as a burn on the operator's skin that may occur when the window unit 203 is separated from the treatment area during the operation may be prevented, and the operation may be performed safely.

Referring to FIGS. 6 and 7, the handle hinge unit 700 may include a hinge shaft unit 710 and a rotation stopper unit 720 that is configured to restrain a rotation angle of the body housing unit 100 which is rotated around the hinge shaft unit 710.

The rotation stopper unit 720 includes a plurality of restraining groove units 721 that are positioned to be space apart from each other on an outer circumferential surface of the hinge shaft unit 710, and includes a stopper protrusion unit 722 which is positioned at either side of the handle unit 110 and the body housing unit 100 and which protrudes to an inner circumferential surface of a shaft hole and which is inserted into the restraining groove unit 721, the stopper protrusion unit 722 being configured to be separated from the restraining groove unit 721 and then to be moved to the next restraining groove unit 721 in a rotational direction when a rotational force equal to or more than a preset rotational force is applied to the stopper protrusion unit 722.

As an example, the stopper protrusion unit 722 includes a stopper ball member 722a that protrudes to the inner circumferential surface of the shaft hole, and includes a stopper spring member 722b elastically supporting the stopper ball member 722a.

In addition, the stopper protrusion unit 722 may be realized in various forms by using a known structure in which the stopper protrusion unit 722 is capable of being separated from a groove and then is capable of being inserted into another groove when a force equal to or more than a preset force is applied thereto, so that a more detailed description thereof will be omitted.

Referring to FIG. 8, the handle hinge unit 700 may include the hinge shaft unit 710 and an angle adjustment motor 730 that is configured to adjust an angle of the body housing unit 100 by rotating the hinge shaft unit 710.

In addition, the handle hinge unit 700 may further include an angle adjustment switch unit 740 positioned at the handle body 112 and configured to control an operation of the angle adjustment motor 730.

The angle adjustment motor 730 is positioned at the hinge shaft unit 710 and is configured to rotate the hinge shaft unit 710, so that the operator may precisely position an angle of the body housing unit 100 at a desired angle.

When the operator controls the angle adjustment switch unit 740 that is positioned at the handle body 112, the angle adjustment motor 730 rotates the hinge shaft unit 710 in a clockwise direction or a counterclockwise direction, so that an angle of the body housing unit 100 may be freely adjusted during the operation.

In addition, another embodiment of the handpiece for ultrasound treatment according to the present disclosure further includes a plurality of contact sensor units 750 positioned at the lower surface of the cartridge housing unit 200 and configured to detect whether the window unit 203 is in contact with the skin. Further, the angle adjustment motor 730 is connected to the plurality of contact sensor units 750, and receives contact signals detected by the plurality of contact sensor units 750 and adjust an angle of the body housing unit 100 so that an entire surface of the window unit 203 is in contact with the skin.

The plurality of contact sensor units 750 may be realized in various forms by using a known contact sensor that detects whether the known contact sensor is in contact with the skin, so that a more detailed description thereof will be omitted.

The plurality of contact sensor units 750 is positioned to be spaced apart from each other along a circumference of the window unit 203, and detect a contact state of the window unit 203. Further, when it is detected that any one of the plurality of contact sensor units 750 is not contacted, the angle adjustment motor 730 receives a non-contact signal and adjusts an angle of the body housing unit 100, thereby allowing the entire surface of the window unit 203 to be in contact with the skin.

Figure 9:
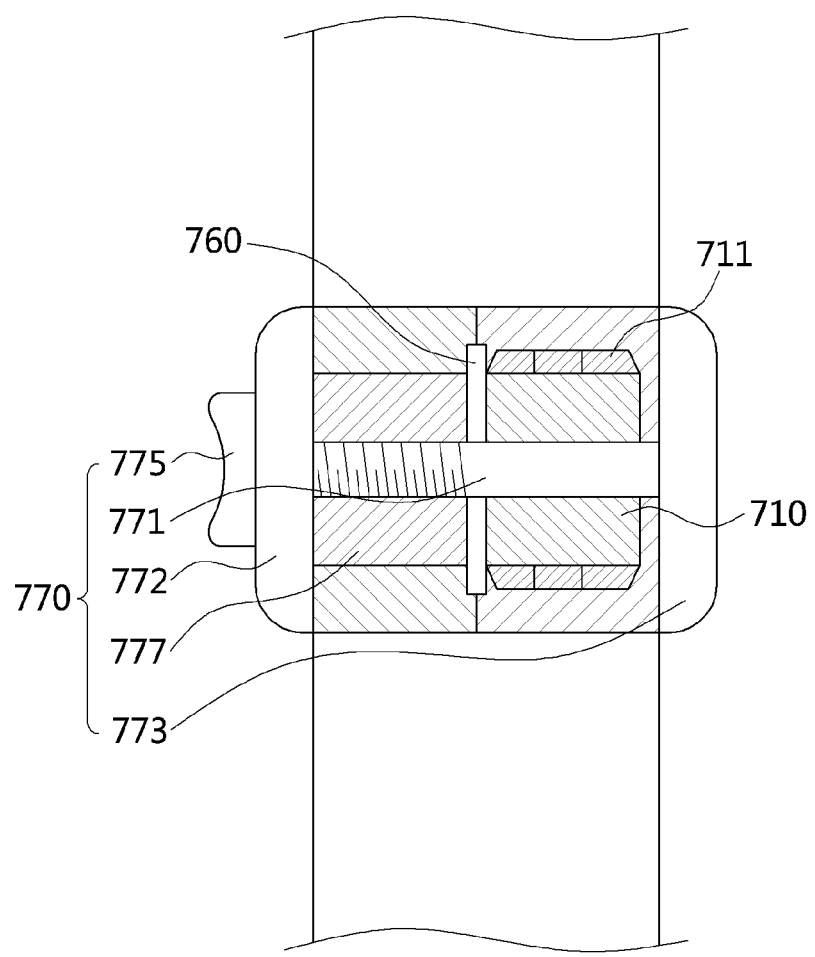
FIG. 9 is a cross-sectional view illustrating another embodiment a handle hinge unit in the handpiece for ultrasound treatment according to the present disclosure.

FIG. 9 is a cross-sectional view illustrating another embodiment of the handle hinge unit 700 of the handpiece for ultrasound treatment according to the present disclosure. Referring to FIG. 9, the handle hinge unit 700 may further include a clearance bushing unit 711 into which the hinge shaft unit 710 is inserted therein and configured to allow the hinge shaft unit 710 to be rotated when a rotational force equal to or more than a preset rotational force is applied to the clearance bushing unit 711.

The clearance bushing unit 711 is coupled to the hinge shaft unit 710 in a tight state, thereby allowing the hinge shaft unit 710 to be rotated when a rotational force equal to or more than the preset rotational force is applied to the clearance bushing unit 711.

In addition, the handle hinge unit 700 may further include a brake pad 760 configured to brake a rotation of the hinge shaft unit 710, and a brake actuation knob unit 770 configured to press the hinge shaft unit 710 with the brake pad 760.

The brake actuation knob unit 770 may include a knob rotary shaft member 771 positioned through the hinge shaft unit 710, a first rotation knob 772 and a second rotation knob 773 that are respectively positioned at opposite end portions of the knob rotary shaft member 771, a pressing member 774 to which the knob rotary shaft member 771 penetrates and is screwed, the pressing member 774 being configured to press or release the brake pad 760 by being moved forward or backward by the rotation of the knob rotary shaft member 771, and a knob handle unit 775 positioned such that the knob handle unit 775 protrudes on the first rotation knob 772.

When the knob handle unit 775 is held and the knob rotary shaft member 771 is rotated in a first direction, the pressing member 774 presses the brake pad 760, so that an angle of the body housing unit 100 may be more firmly fixed.

In addition, when the knob handle unit 775 is held and the knob rotary shaft member 771 is rotate in an opposite direction, a state in which the brake pad 760 is pressed by the pressing member 774 is released. Therefore, by applying a rotational force equal to or more than the preset rotational force, the body housing unit 100 is rotated around the hinge shaft unit 710, so that an angle of the body housing unit 100 may be adjusted.

In the present disclosure, an energy is uniformly and evenly applied to a treatment area by moving a focus of ultrasonic waves in a plane at a uniform depth in the skin, and the focus of the ultrasonic waves is formed in a circular shape having a constant radius at the uniform depth in the skin, so that treatment performance may be increased by uniformly and evenly applying the energy within the radius.

In addition, in the present disclosure, a structure in which a focus of ultrasonic waves generated from the ultrasonic transducer unit is moved in a circle on the same plane is simplified, and a size of the handpiece for ultrasound treatment is miniaturized, so that ultrasound treatment of local areas of a patient's skin, such as a portion below the eyes is capable of being performed.

It is to be understood that the present disclosure is not limited to the above described embodiments but may be variously modified and embodied within the scope of the present disclosure without departing from the gist of the present disclosure.

The invention claimed is:

1. A therapeutic ultrasound generation device comprising:
a cartridge housing unit;
an ultrasonic transducer unit positioned in the cartridge housing unit and disposed inclined with respect to a direction of a rotational central axis direction, thereby being configured to generate ultrasonic waves in an inclined direction;
an inclined block unit positioned in the cartridge housing unit, having an inclined surface on a lower surface thereof, and supporting an upper surface of the ultrasonic transducer unit, thereby positioning the ultrasonic transducer unit to be inclined with respect to the rotational central axis direction;
a rotating motor configured to rotate the inclined block unit,
wherein a ball joint unit to which the ultrasonic transducer unit is rotatably coupled is protrudingly positioned on a center of the inclined block unit, a plurality of support ball members configured to be rotated while supporting the upper surface of the ultrasonic transducer unit is protrudingly positioned on the lower surface of the inclined block unit, and the ultrasonic transducer unit is coupled to a ball body of the ball joint unit and the upper surface of the ultrasonic transducer unit is supported while being in contact with the plurality of support ball members, so that the ultrasonic transducer unit is positioned inclined,
a torsion bar member which has a first end portion connected to the ultrasonic transducer unit and which has a second end portion connected to the cartridge housing unit,
wherein the torsion bar member comprises:
a first mounting unit mounted on the ultrasonic transducer unit;
a second mounting unit mounted on an inner surface of the cartridge housing unit; and
a torsion spring unit having opposite end portions thereof respectively connected to the first mounting unit and the second mounting unit, the torsion spring unit absorbing shock with torsional elasticity, and
wherein the torsion bar member is provided as a pair of torsion bar members positioned to be facing each other, and in the pair of torsion bar members, each torsion spring unit is formed with a shape and length to use torsional elasticity and absorb shock that is generated when the ultrasonic transducer unit is continuously inclined in all directions of 360 degrees.

2. A therapeutic ultrasound generation device comprising:
a cartridge housing unit;
an ultrasonic transducer unit positioned in the cartridge housing unit and disposed inclined with respect to a direction of a rotational central axis direction, thereby being configured to generate ultrasonic waves in an inclined direction;
an inclined block unit positioned in the cartridge housing unit, having an inclined surface on a lower surface thereof, and supporting an upper surface of the ultrasonic transducer unit, thereby positioning the ultrasonic transducer unit to be inclined with respect to the rotational central axis direction;
a rotating motor configured to rotate the inclined block unit; and
a torsion bar member which has a first end portion connected to the ultrasonic transducer unit and which has a second end portion connected to the cartridge housing unit,
wherein the torsion bar member comprises:
a first mounting unit mounted on the ultrasonic transducer unit;
a second mounting unit mounted on an inner surface of the cartridge housing unit; and
a torsion spring unit having opposite end portions thereof respectively connected to the first mounting unit and the second mounting unit, the torsion spring unit absorbing shock with torsional elasticity, and
wherein the torsion bar member is provided as a pair of torsion bar members positioned to be facing each other, and in the pair of torsion bar members, each torsion spring unit is formed with a shape and length to use torsional elasticity and absorb shock that is generated when the ultrasonic transducer unit is continuously inclined in all directions of 360 degrees.

3. The therapeutic ultrasound generation device of claim 2, wherein the torsion spring unit is formed such that the torsion spring unit has at least one of a bent unit or a curved unit.

4. The therapeutic ultrasound generation device of claim 2, wherein the ultrasonic transducer unit is configured to be continuously inclined in all directions of 360 degrees with respect to the rotational central axis direction, so that a focus of ultrasonic waves generated from the ultrasonic transducer unit is moved such that the focus is formed in a circular shape on the same plane.

* * * * *